United States Patent
Yeom

(10) Patent No.: US 10,149,742 B2
(45) Date of Patent: Dec. 11, 2018

(54) METHOD OF ASSEMBLING A DENTAL IMPLANT

(71) Applicant: Myong Hee Yeom, Daejeon (KR)

(72) Inventor: Myong Hee Yeom, Daejeon (KR)

( * ) Notice: Subject to any disclaimer, the term of this patent is extended or adjusted under 35 U.S.C. 154(b) by 409 days.

(21) Appl. No.: 14/941,569

(22) Filed: Nov. 14, 2015

(65) Prior Publication Data

US 2016/0067015 A1    Mar. 10, 2016

Related U.S. Application Data

(62) Division of application No. 13/583,831, filed as application No. PCT/KR2011/007199 on Sep. 29, 2011, now abandoned.

(30) Foreign Application Priority Data

May 26, 2011 (KR) .................. 10-2011-0050035

(51) Int. Cl.
*A61C 8/00*     (2006.01)
*A61C 13/00*    (2006.01)

(52) U.S. Cl.
CPC ............ *A61C 8/0068* (2013.01); *A61C 8/006* (2013.01); *A61C 13/0022* (2013.01); *Y10T 29/49568* (2015.01)

(58) Field of Classification Search
CPC . A61C 13/0004; A61C 13/0006; A61C 13/12; A61C 13/0022; A61C 8/006; A61C 8/0068; A61C 5/10; A61C 7/00; A61C 13/00; Y10T 29/49568; Y10T 29/49567
See application file for complete search history.

(56) References Cited

U.S. PATENT DOCUMENTS

| | | | |
|---|---|---|---|
| 4,713,003 A * | 12/1987 | Symington | A61C 8/0022 433/173 |
| 4,995,810 A * | 2/1991 | Soderberg | A61C 8/0089 433/141 |
| 5,169,308 A | 12/1992 | Kvist | |
| 5,213,502 A | 5/1993 | Daftary | |

(Continued)

FOREIGN PATENT DOCUMENTS

| KR | 10-2006-0116300 A | 11/2006 |
|---|---|---|
| KR | 10-2009-0090894 A | 8/2009 |

(Continued)

*Primary Examiner* — Sarang Afzali
(74) *Attorney, Agent, or Firm* — Drinker Biddle & Reath LLP

(57) ABSTRACT

An abutment connecting a crown that forms an external form of an artificial tooth to a fixture embedded in a gum of a human, having a body, a combination portion formed at an end of the body and combined with the fixture, a threaded portion formed at the body and penetrating through the body, a fixing screw being inserted into the threaded portion to couple the body to a processing device or a jig, a coupling hole formed at the body and penetrating through the body, a coupling unit being inserted into the coupling hole to connect the body and the fixture, and a sectional surface formed at an opposite portion to the combination portion and connected to the processing device or the jig, to position the body in the processing device or in the jig when the body is coupled to the processing device or the jig.

6 Claims, 4 Drawing Sheets

(56) References Cited

U.S. PATENT DOCUMENTS

| | | | |
|---|---|---|---|
| 5,733,122 A | 3/1998 | Gordon | |
| 5,782,918 A | 7/1998 | Klardie et al. | |
| 6,287,116 B2 | 9/2001 | Lazzara | |
| 6,312,260 B1 * | 11/2001 | Kumar | A61C 8/008 206/368 |
| 6,663,388 B1 | 12/2003 | Schar et al. | |
| 7,393,210 B2 | 7/2008 | Kim | |
| 2002/0123022 A1 | 9/2002 | Pilla et al. | |
| 2006/0292527 A1 | 12/2006 | Basler et al. | |
| 2008/0254413 A1 | 10/2008 | Gampert | |
| 2009/0123890 A1 | 5/2009 | Purga et al. | |
| 2009/0274994 A1 | 11/2009 | Jung et al. | |
| 2010/0068674 A1 | 3/2010 | Zucker | |
| 2011/0053114 A1 | 3/2011 | Shimoda | |
| 2011/0065065 A1 | 3/2011 | Mormann | |
| 2011/0171603 A1 | 7/2011 | Kim | |
| 2012/0237902 A1 | 9/2012 | Maniscalco | |
| 2012/0251979 A1 | 10/2012 | Karim et al. | |
| 2012/0308960 A1 | 12/2012 | Mashio et al. | |
| 2014/0017632 A1 | 1/2014 | Ryu et al. | |

FOREIGN PATENT DOCUMENTS

| | | |
|---|---|---|
| KR | 10-2010-0048968 A | 5/2010 |
| KR | 10-0981463 B1 | 9/2010 |
| KR | 10-2010-0118543 A | 11/2010 |
| WO | 95/21589 A1 | 8/1995 |
| WO | 2010/072458 A1 | 7/2010 |

\* cited by examiner

METHOD OF ASSEMBLING A DENTAL IMPLANT

CROSS-REFERENCE TO RELATED APPLICATIONS

This application is a divisional of U.S. patent application Ser. No. 13/583,831 filed Sep. 30, 2013, now abandoned, which is the U.S. national phase of International Patent Application No. PCT/KR2011/007199 filed Sep. 29, 2011, which claims the benefit of Korean Patent Application No. 10-2011-0050035 filed May 26, 2011, the entire content of which is incorporated herein by reference.

FIELD OF THE INVENTION

Embodiments relate to an abutment for implant, and more particularly to the shape of an abutment which allows a customized abutment responding to characteristics of individual teeth of each patient to be obtained by precise processing.

BACKGROUND

An implant is an artificial tooth implanted into an alveolus when a tooth is lost or damaged. The implant has the following advantages: it allows only a lost or damaged tooth to be replaced without sacrificing adjacent teeth, it allows the artificial tooth to function like a natural tooth, it looks and feels like a natural tooth, it allows a patient to speak clearly after an operation, and it quickly improves the patient's oral health.

A general implant comprises a fixture embedded in the gum, an abutment fixed to the fixture by using a screw, and a crown fixed onto the abutment so as to give an external form of an artificial tooth. At this case, the abutment supports the crown.

Here, the abutment (hereinafter, referred to as a processing object) functions to transfer a load from the crown to the fixture, and hence to the jaw bone. For this reason, the processing object should be manufactured considering not only a size, a shape, and a contour of an artificial tooth, but also the occlusion with adjacent teeth and an opposing tooth (an upper tooth or lower tooth), and dental characteristics, conditions of the gum, and the gum line of an individual patient.

As for the processing object of the implant, customized products manufactured so as to correspond to patient's teeth are preferred to generic products having fixed sizes.

SUMMARY

An embodiment of the invention provides an abutment for implant which improves processing precision of the abutment by allowing the abutment to be precisely and accurately positioned and fixed in the correct position in a processing device or a jig when the abutment is processed to become a customized abutment which requires high precision.

In one embodiment, there is an abutment connecting a crown that forms an external form of an artificial tooth to a fixture embedded in a gum of a human and comprises a body, a combination portion formed at an end of the body and combined with the fixture, a threaded portion formed at the body and penetrating through the body, a fixing screw being inserted into the threaded portion to couple the body to a processing device or a jig, a coupling hole formed at the body and penetrating through the body, a coupling unit being inserted into the coupling hole to connect the body and the fixture, and a sectional surface formed at an opposite portion to the combination portion and connected to the processing device or the jig, to position the body in the processing device or in the jig when the body is coupled to the processing device or the jig.

The abutment may further comprise an installation portion formed at another end of the body and installing the body in the processing device or the jig, and the sectional surface may be formed at the installation portion.

The installation portion may be tapered as the sectional surface is far from the body.

The abutment may further comprise a recess portion formed between the body and the installation portion.

The installation portion may have an outer diameter smaller than an outer diameter of the body.

The installation portion may have a surface of a D shape or a polygonal shape.

The sectional surface may be formed at a portion of a side of the body.

The body may have a surface of a letter D shape or a polygonal shape, which is in contact with the sectional surface.

BRIEF DESCRIPTION OF THE DRAWINGS

The accompanying drawings, which are included to provide a further understanding of the invention and are incorporated in and constitute a part of this specification, illustrate embodiments of the invention and together with the description serve to explain the principles of the invention. In the drawings.

DETAILED DESCRIPTION OF THE INVENTION

Hereinafter, embodiments of the invention will be described in detail with reference to the accompanying drawings.

An abutment for implant according to each embodiment of the invention is for producing a final abutment which connects a fixture (such as the fixture 11 shown in FIG. 1D) embedded in the gum to a crown forming an external form of an artificial tooth.

Figure 1A:
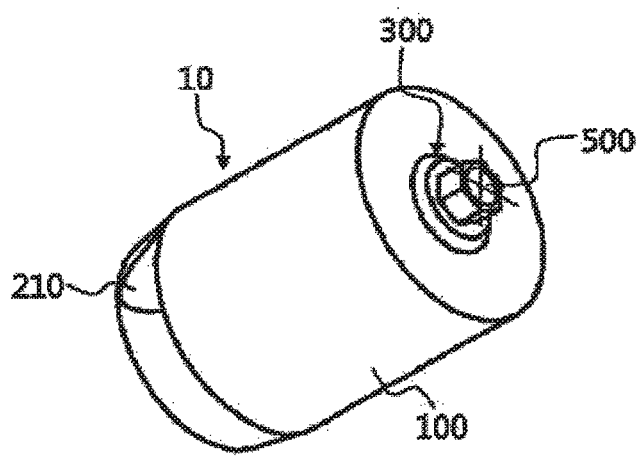
FIG. 1A is an illustration of an abutment for an implant oriented to show a combination portion, according to an embodiment of the invention.
Figure 1B:
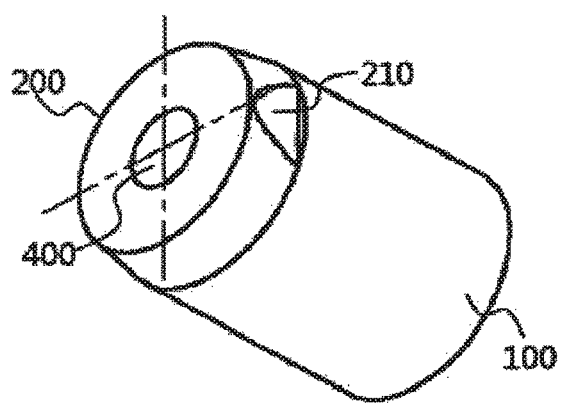
FIG. 1B is an illustration of an abutment for an implant oriented to show an opening of a threaded portion, according to an embodiment of the invention.
Figure 1C:
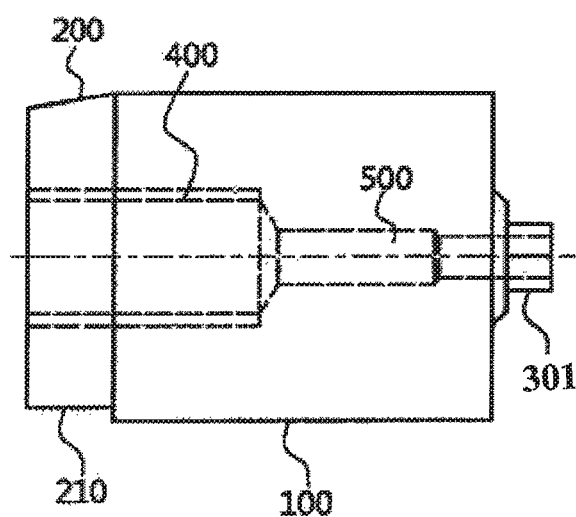
FIG. 1C is a cross-section illustration of an abutment for an implant, according to an embodiment of the invention.
Figure 1D:
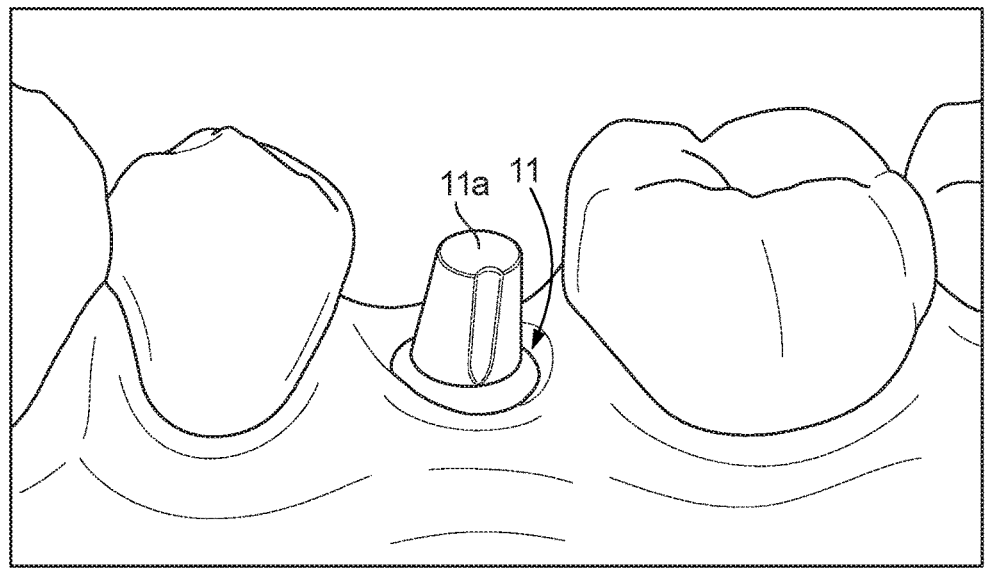
FIG. 1D is an illustration of an example fixture.

FIGS. 1A, 1B and 1C are diagrams illustrating an abutment for implant according to an embodiment of the invention, respectively.

Figure 1E:
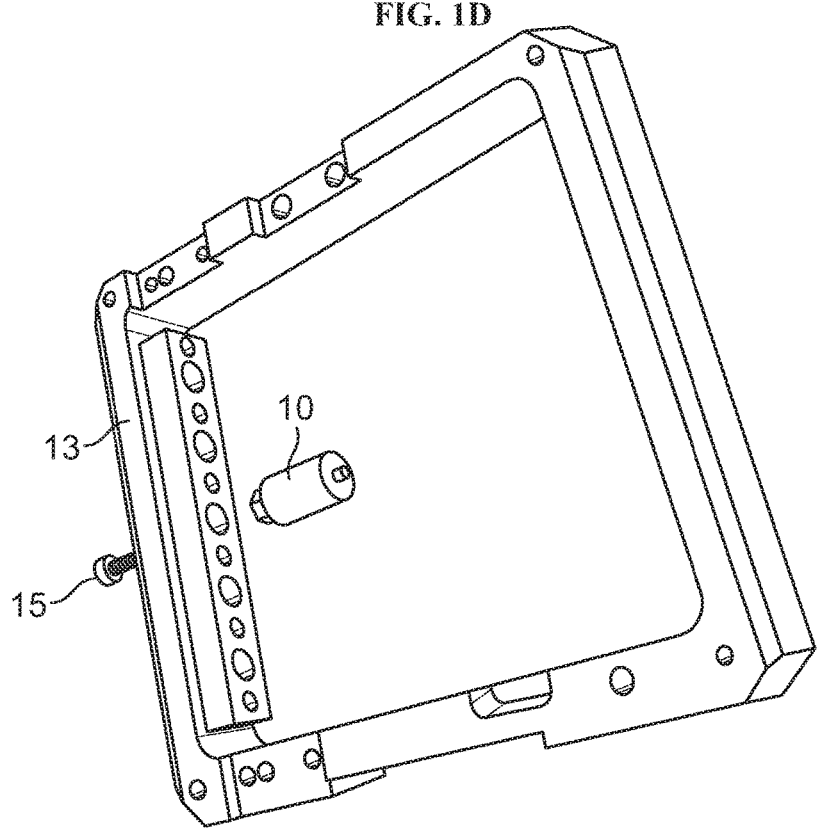
FIG. 1E is an illustration of an example jig used in conjunction with various embodiments.

As illustrated in FIGS. 1A-1C, the abutment 10 for implant according to the embodiment comprises a body 100 having a cylindrical shape, an installation portion 200 which is integrally formed with an end of the body 100 and serves as a portion to install the body 100 in a processing device or in a jig 13 (FIG. 1E) when a customized abutment (that is, a final abutment) is produced by processing the body 100, a combination portion 300, having a base 301, formed at the other end of the body 100 so as to be combined with a fixture, a threaded portion 400, having an opening 401, formed to penetrate through the installation portion 200 and to pass through a portion of the body 100 so that a fixing screw 15 (FIG. 1E) can be inserted into the threaded portion and thus the body 100 is fixed to the processing device or the jig, and a coupling hole 500 which is formed to penetrate through the body 100 and the combination portion 300 in a longitudinal direction of the body 100 so that a coupling unit 11a (FIG. 1D) used to couple the body 100 to the fixture 11 can be inserted into the coupling hole 500.

The installation portion 200 is tapered to an outside portion of the body 100, that is, from the body 100 to an end of the installation portion 200. Thus, the installation portion 200 is tapered as a sectional surface 210 (described below) is far from the body 100.

Thereby, an external diameter of the installation portion 200 is changed from the body 100 to the end of the installation portion 200. For example, as shown in FIGS. 1A and 1B, the external diameter of installation portion 210 decreases from the body 100 to the end of the installation portion 200.

The installation portion 200 further comprises a sectional surface 210 (that is, a cut portion) used for positioning when the installation portion 200 is coupled to the processing device or the jig. The sectional surface 210 is formed by cutting a part of the installation portion 200. The sectional surface 210 is formed at a portion of a side of the installation portion 200.

Alternatively, the sectional surface 210 may be plural. In this case, at least two sectional surfaces 210 formed at at least two portions of the side of the installation portion 200 have different shaped from each other, or all of the section surfaces 210 may have the same shape as each other.

Thereby, the installation portion 200, that is, a surface (for example, a bottom surface) of the installation portion 200 has a polygonal shape or a letter D shape, and thus, a planar shape of the installation portion 200 is also a polygonal shape or a letter D shape. In the installation portion 200, the bottom surface of the installation portion 200 is opposite a surface contacting to the body 100.

The threaded portion 400 has threads corresponding to threads of a fixing screw.

As described above and shown in FIG. 1C, the threaded portion 400 is formed by penetrating through a portion of the body 100 as well as the installation portion 200 in the longitudinal direction of the body 100. Thereby, the threaded portion 400 is formed at the installation portion 200 and the body 100.

As described above and shown in FIG. 1C, the coupling hole 500 is formed by penetrating through a portion of the body 100 as well as the combination portion 300. Thereby, the coupling hole 500 is formed at the combination portion 300 and the body 100.

Figure 2A:
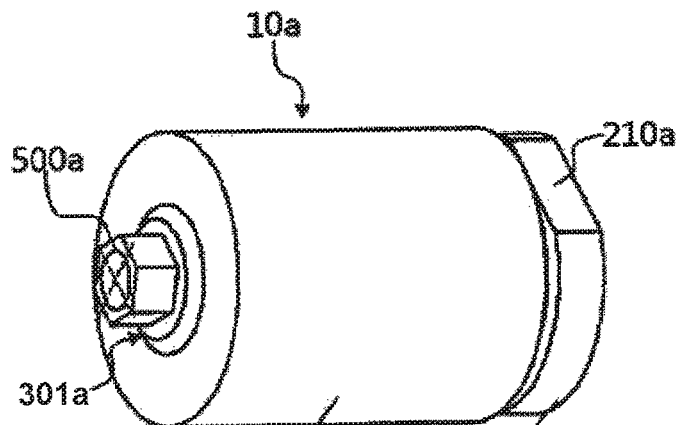
FIG. 2A is an illustration of an abutment for an implant oriented to show a combination portion, according to an embodiment of the invention.
Figure 2B:
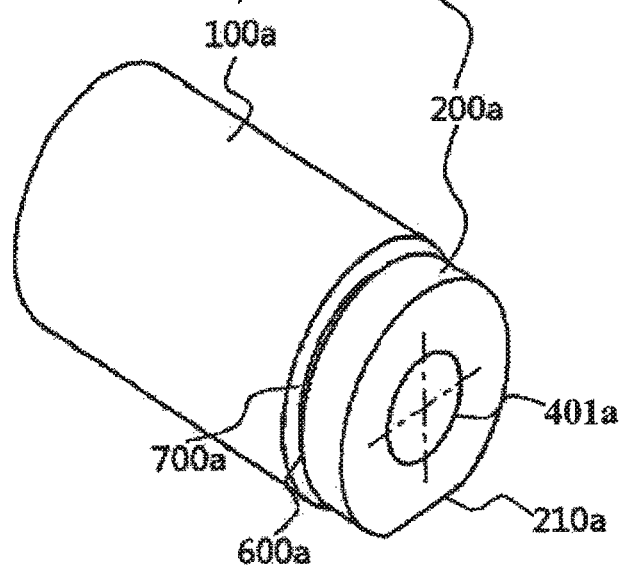
FIG. 2B is an illustration of an abutment for an implant oriented to show an opening of a threaded portion, according to an embodiment of the invention.
Figure 2C:
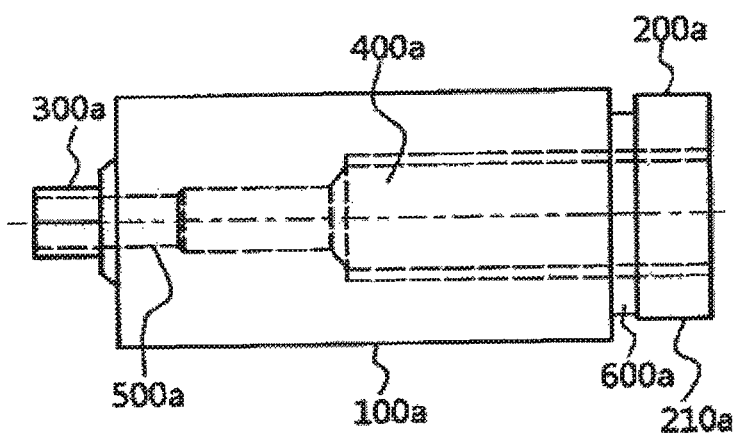
FIG. 2C is a cross-section illustration of an abutment for an implant, according to an embodiment of the invention.

FIGS. 2A, 2B and 2C are diagram illustrating an abutment for implant according to another embodiment of the invention, respectively.

As illustrated in FIGS. 2A-2C, an abutment 10a for implant according to the embodiment of the invention comprises a body 100a, an installation portion 200a, a combination portion 300a, having a base 301a, a recess portion 600a, a threaded portion 400a, having an opening 401a, and a coupling hole 500a.

The installation portion 200a is integrally formed with an end of the body 100a and is used to install the body 100a in a processing device or in a jig when the body 100a is processed to produce a customized abutment (that is, a final abutment).

The combination portion 300a is formed at the other end of the body 100a so as to be combined with the fixture.

The recess portion 600a is formed between the body 100a and the installation portion 200a to provide an installation reference plane 700a of the body 100a when the body 100a is fixed.

Thereby, a portion of the installation portion 200a is separated from the body 100a by the recess portion 600a.

Unlike the installation portion 200 of FIG. 1, the installation portion 200a of the embodiment has the same external diameter as a position of the installation portion 200a is changed from the body 100a to the end of the installation portion 200a along the longitudinal direction of the body 100a. That is, the installation portion 200a is not tapered.

The threaded portion 400a is formed to penetrate through the installation portion 200a and to pass through to a midway portion of the body 100a in the longitudinal direction of the body 100a so that a fixing screw used to fix the body 100 to the processing device or the jig may be inserted into the threaded portion 400a.

As described above and shown in FIG. 2C, the threaded portion 400a is formed by penetrating through a portion of the body 100a as well as the installation portion 200a and, thereby, the threaded portion 400a is formed at the installation portion 200a and the body 100a.

The coupling hole 500a is formed to penetrate through the body 100a and the combination portion 300a along the longitudinal direction of the body 100a so that a coupling unit used to couple the body 100a to the fixture may be inserted into the coupling hole 500a.

Thereby, as described above and shown in FIG. 2C, the coupling hole 500a is formed by penetrating through a portion of the body 100a as well as the combination portion 300a. Thus, the coupling hole 500a is formed at the combination portion 300a and the body 100a.

The installation portion 200a is formed to be smaller than an outer diameter of the body 100a and, thereby, the installation portion 200a has an outer diameter smaller than the outer diameter of the body 100a. Moreover, the installation portion 200a has the sectional surface 210a (that is, a cut portion) used to position the body 100a in the processing device or the jig when the body 100a is coupled to the processing device or the jig.

The sectional surface 210a is formed by cutting a part of the installation portion 200a. The sectional surface 210a is formed at a portion of a side of the installation portion 200a.

Alternatively, the sectional surface 210a may be plural. In this case, at least two sectional surfaces 210a formed at at least two portions of the side of the installation portion 200a have different shaped from each other, or all of the section surfaces 210a may have the same shape as each other.

Thereby, the installation portion 200a, that is, a surface (for example, a bottom surface) of the installation portion 200a has a polygonal shape or a letter D shape and thus, a planar shape of the installation portion 200 is also a polygonal shape or a letter D shape. In the installation portion 200a, the bottom surface of the installation portion 200a is opposite a surface contacting to the body 100a.

Figure 3A:
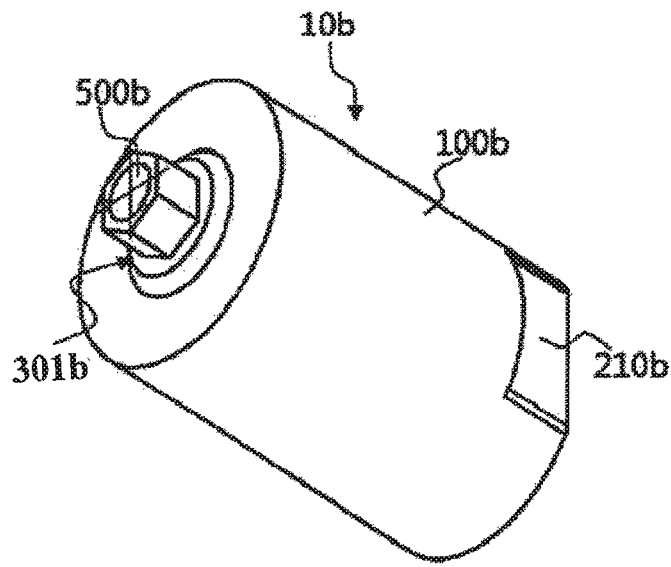
FIG. 3A is an illustration of an abutment for an implant oriented to show a combination portion, according to an embodiment of the invention.
Figure 3B:
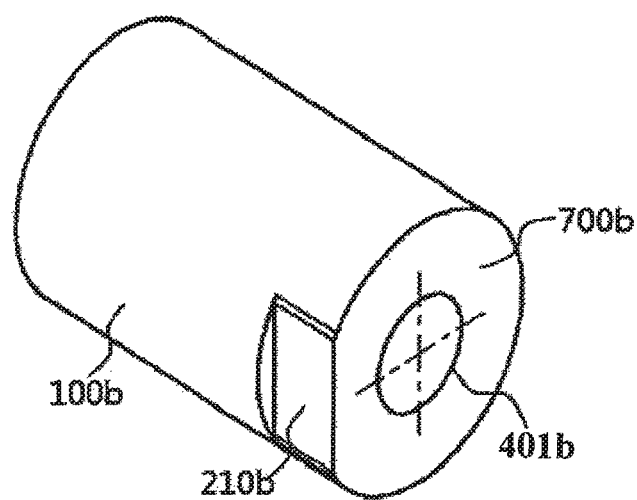
FIG. 3B is an illustration of an abutment for an implant oriented to show an opening of a threaded portion, according to an embodiment of the invention.
Figure 3C:
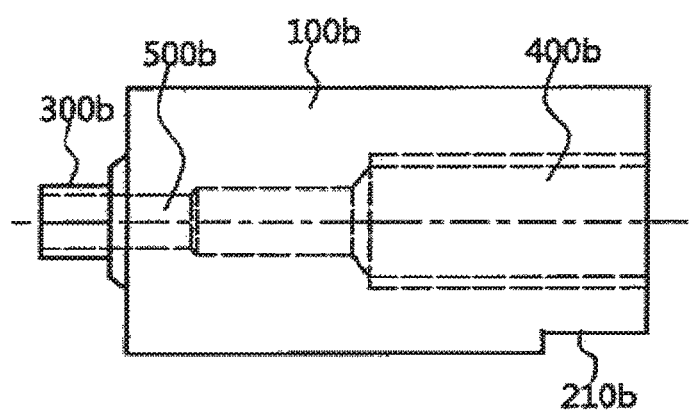
FIG. 3C is a cross-section illustration of an abutment for an implant, according to an embodiment of the invention.

Moreover, the threaded portion 400a has threads corresponding to threads of the fixing screw. FIGS. 3A, 3B and 3C are diagrams illustrating an abutment for implant according to another embodiment of the invention.

As illustrated in FIG. 3, an abutment 10b for implant according to an embodiment of the invention comprises a body 100b, a combination portion 300b, having a base 301b, formed at a portion of the body 100b so as to be combined with a fixture, a threaded portion 400b, having an opening 401b, formed to extend from an installation reference plane 700b to a midway portion of the body 100b in a manner of passing through the body 100b in a longitudinal direction of the body 100b so that a fixing screw 15 used to couple the body 100b to a processing device or a jig 13 (depicted in FIG. 1E) may be inserted into the threaded portion 400b, and a coupling hole 500b formed to penetrate through the body 100band the combination portion 300b the longitudinal direction so that a coupling unit used to couple the body 100b to the fixture may be inserted into the coupling hole 500b.

Moreover, the other end of the body 100b in which the combination portion 300b is located comprises a sectional surface 210b used to position the body 100b in the processing device or in the jig.

The sectional surface 210b is formed by cutting a part of the body 100b. The sectional surface 210b is formed at a portion of a side of the body 100b.

Alternatively, the sectional surface 210b may be plural. In this case, at least two sectional surfaces 210b formed at at least two portions of the side of the body 100b have different shaped from each other, or all of the section surfaces 210b may have the same shape as each other.

Thereby, the body 100b, that is, a surface (for example, a bottom surface) of the other end of the body 100b has a polygonal shape or a letter D shape, and thus, a planar shape of the body 100b is also a polygonal shape or a letter D shape. In the installation portion 200a, the bottom surface of the body 100b is opposite the combination portion 300a and the coupling hole 500b formed at one end of the body 100b.

Moreover, the threaded portion 400b preferably has threads corresponding to threads of the fixing screw.

As described above and shown in FIG. 3C, the threaded portion 400b is formed by penetrating through a portion of the body 100b, and, thereby, the threaded portion 400b is formed in the body 100a.

As described above and shown in FIG. 3C, the coupling hole 500b is formed by penetrating through a portion of the body 100b and the combination portion 300b. Thereby, the coupling hole 500b is also formed at the body 100b and the combination portion 300b.

Based on the above description referring to FIGS. 1 to 3, each abutment 10, 10a or 10b comprises the sectional surface 210, 210a or 210b formed at an opposite portion to the combination portion 310, 310a or 310b and connected to the processing device or the jig, to position the body 100, 100a or 100b in the processing device or in the jig when the body 100, 100a or 100b is coupled to the processing device or the jig.

Also, referring to FIGS. 1 and 2, each of the installation portions 200 and 200a is formed at each of another ends of the bodies 100 and 100a and installs each body 100 or 100a in the processing device or the jig, and the sectional surface 210 and 210a is formed at the installation portion 200 and 200a.

As described above, when the customized abutment of each embodiment, which is required to be precisely processed, is produced using an abutment 10, 10a, or 10b, the abutment 10, 10a, or 10b for implant according to each embodiment is precisely and accurately installed and fixed in the correct position in a simple manner in the processing device or the jig by using the threaded portions 400, 400a, or 400b and fixing screws horizontally coupled to an abutment 10, 10a, or 10b installed in the processing device or the jig, without using a way of clamping or gripping the outer surface of the abutments 10, 10a or 10b. Accordingly, it is possible to improve throughput and precision when the customized abutments are produced.

In each abutment 10, 10a, or 10b for implant according to the embodiments of the invention, the installation portion 200 or 200a or the body 100b is formed to have the sectional surfaces 210, 210a, and 210b of the letter D shape or a polygonal shape. At this time, each of the sectional surfaces 210, 210a, and 210b is formed in at least one part of the installation portions 200 and 200a or the body 100b.

Each of the installation portion 200 or 200a is opposite the combination portion 300, 300a, 300b, and the part of the body 100b, on which the sectional surface 210b is formed, is adjacent to the end of the body 100b opposite the installation portion 200b.

Thereby, the sectional surfaces 210, 210a and 210b are formed at an opposite portion to the combination portion 300, 300a and 300b, and the opposite portion is a portion near where the threaded portions 400, 400a and 400b are formed.

Therefore, as compared with an abutment which is circular in shape, when each of the abutments 10, 10a, and 10b is coupled to the processing device or the jig by using a fixing screw, the positioning of each abutment 10, 10a, or 10b may be conveniently and easily performed by the sectional surfaces 210, 201a and 210b.

What is claimed is:

1. A method of assembling a dental implant, the method comprising:
   providing an abutment of a dental implant having a cylindrical body;
   forming an installation portion on one end of the body;
   forming a threaded portion by penetrating through the installation portion;
   forming a combination portion on another and opposite end of body;
   forming a coupling hole to penetrate through the combination portion;
   coupling the body to a processing device or jig with a fixing screw inserted into the threaded portion formed within the body;
   processing the abutment while the abutment is still coupled to the processing device or jig to create a customized abutment corresponding to a shape and a contour of an artificial tooth; and
   inserting a coupling unit of a dental fixture embedded in a gum of a human into the coupling hole formed in the customized abutment, thereby connecting the customized abutment to the dental fixture.

2. The method of claim 1, wherein the installation portion comprises a sectional surface, the method further comprising using the sectional surface for positioning the abutment while coupling the abutment to the processing device or jig.

3. The method of claim 2, further comprising forming the sectional surface by cutting a part of the installation portion.

4. The method of claim 3, wherein forming the sectional surface comprises forming the sectional surface to have a shape of the uppercase alphabet letter D.

5. The method of claim 3, wherein forming the sectional surface comprises forming the sectional surface to have a polygonal shape.

6. The method of claim 1,
wherein the coupling hole is penetrated through the combination portion in a longitudinal direction; and
the threaded portion is formed to extend from an installation reference plane to a midway portion of the body in the longitudinal direction.

\* \* \* \* \*